(12) United States Patent
Furuno et al.

(10) Patent No.: US 6,817,997 B2
(45) Date of Patent: Nov. 16, 2004

(54) LASER TREATMENT APPARATUS

(75) Inventors: Takahiro Furuno, Gamagori (JP); Wataru Niwa, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/080,688

(22) Filed: Feb. 25, 2002

(65) Prior Publication Data

US 2002/0120315 A1 Aug. 29, 2002

(30) Foreign Application Priority Data

Feb. 28, 2001 (JP) .................................. 2001-056046

(51) Int. Cl.[7] .............................................. A61B 18/18
(52) U.S. Cl. .............................................. 606/9; 606/12
(58) Field of Search .......................... 606/9, 1, 12, 27, 606/28, 31; 607/101, 102

(56) References Cited

U.S. PATENT DOCUMENTS

| | | | |
|---|---|---|---|
| 4,813,412 A | | 3/1989 | Yamazaki et al. |
| 5,057,104 A | * | 10/1991 | Chess .............................. 606/9 |
| 5,344,418 A | * | 9/1994 | Ghaffari ........................ 606/9 |
| 5,486,172 A | * | 1/1996 | Chess ........................... 606/20 |
| 6,015,404 A | | 1/2000 | Altshuler et al. |
| 6,059,820 A | | 5/2000 | Baronov |
| 6,104,959 A | | 8/2000 | Spertell |
| 6,273,884 B1 | * | 8/2001 | Altshuler et al. ............... 606/9 |
| 2001/0007068 A1 | * | 7/2001 | Ota et al. ....................... 606/9 |
| 2002/0049432 A1 | * | 4/2002 | Mukai ............................ 606/9 |
| 2002/0068926 A1 | * | 6/2002 | Ota et al. ....................... 606/9 |

FOREIGN PATENT DOCUMENTS

EP         1 057 454 A2    12/2000

* cited by examiner

Primary Examiner—Michael Peffley
(74) Attorney, Agent, or Firm—Oliff & Berridge, PLC

(57) ABSTRACT

A laser treatment apparatus for performing treatment on a treatment part of a skin by irradiating the part with a laser beam for treatment is disclosed. The apparatus includes: a window having an optical property of transmitting the treatment beam, the window being brought into contact with the skin for laser irradiation; a window cooling unit; a contact-state detector which detects a contact state of the window with the skin; and a controller which changes a cooling control temperature of the cooling unit from a predetermined first temperature which is previously set higher than 0° C. to a predetermined second temperature lower than the first temperature when the contact-state detector detects that the window is in contact with the skin.

26 Claims, 6 Drawing Sheets

LASER TREATMENT APPARATUS

BACKGROUND OF THE INVENTION

1. Field of the Invention

The present invention relates to a laser treatment apparatus for performing treatment by irradiating a treatment part (an affected part) of a skin with a laser beam for treatment.

2. Description of Related Art

A laser treatment apparatus which is used in dermatology clinics or hospital's dermatology departments, for example, a laser apparatus for depilation, performs laser irradiation while cooling an irradiation part (a skin) in order to prevent a burn on the skin which may be caused by generation of heat at the time of laser irradiation or to alleviate a pain which may be caused by the laser irradiation. As a cooling means to cool the skin, there has been known a means of cooling a window which transmits a laser beam for treatment and is brought into contact with the skin, thus cooling the skin.

As a difference in temperature between the window cooled and the outside air becomes larger, however, dew condensation likely occurs on a surface of the window. If the window in this state is further cooled, a problem that the condensed water (dew) freezes may arise. The condensation and freeze occurring on the window surface tends to reduce observability of the treatment part through the window, and to decrease transmittance of the treatment laser beam, causing a lowering of laser power. To the contrary, if the cooling temperature for the window is set higher for the purpose of preventing the occurrence of condensation and freeze, the skin could not be sufficiently cooled.

SUMMARY OF THE INVENTION

The present invention has been made in view of the above circumstances and has an object to overcome the above problems and to provide a laser treatment apparatus capable of performing laser irradiation while cooling an affected part and simultaneously preventing occurrence of dew condensation and freeze on a window surface.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatment on a treatment part of a skin by irradiating the part with a laser beam for treatment, the apparatus including: a window having an optical property of transmitting the treatment beam, the window being brought into contact with the skin for laser irradiation; a window cooling unit; contact-state detecting means which detects a contact state of the window with the skin; and control means which changes a cooling control temperature of the cooling unit from a predetermined first temperature which is previously set higher than 0° C. to a predetermined second temperature lower than the first temperature when the contact-state detecting means detects that the window is in contact with the skin.

According to another aspect of the present invention, there is provided a laser treatment apparatus for performing treatment on a treatment part of a skin by irradiating the part with a laser beam for treatment, the apparatus including: a window having an optical property of transmitting the treatment beam, the window being brought into contact with the skin for laser irradiation; a window cooling unit; first input means which inputs an operation signal representing that preparation for laser irradiation is completed; and control means which changes a cooling control temperature of the cooling unit from a predetermined first temperature which is previously set higher than 0° C. to a predetermined second temperature lower than the first temperature when the operation signal is input by the first input means.

Furthermore, according to another aspect of the present invention, there is provided a laser treatment apparatus for performing treatment on a treatment part of a skin by irradiating the part with a laser beam for treatment, the apparatus including: a window having an optical property of transmitting the treatment beam, the window being brought into contact with the skin for laser irradiation; a window cooling unit; irradiation command signal input means which inputs a laser irradiation command signal; temperature change signal input means which inputs a temperature changing signal to change a cooling control temperature of the cooling unit from a predetermined first temperature higher than 0° C. to a predetermined second temperature lower than the first temperature; and control means which changes the cooling control temperature from the first temperature to the second temperature in response to the temperature changing signal input by the temperature change signal input means and returns the cooling control temperature to the first temperature when no irradiation command signal is input by the irradiation command signal input means within a predetermined waiting time after the cooling control temperature is changed to the second temperature.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
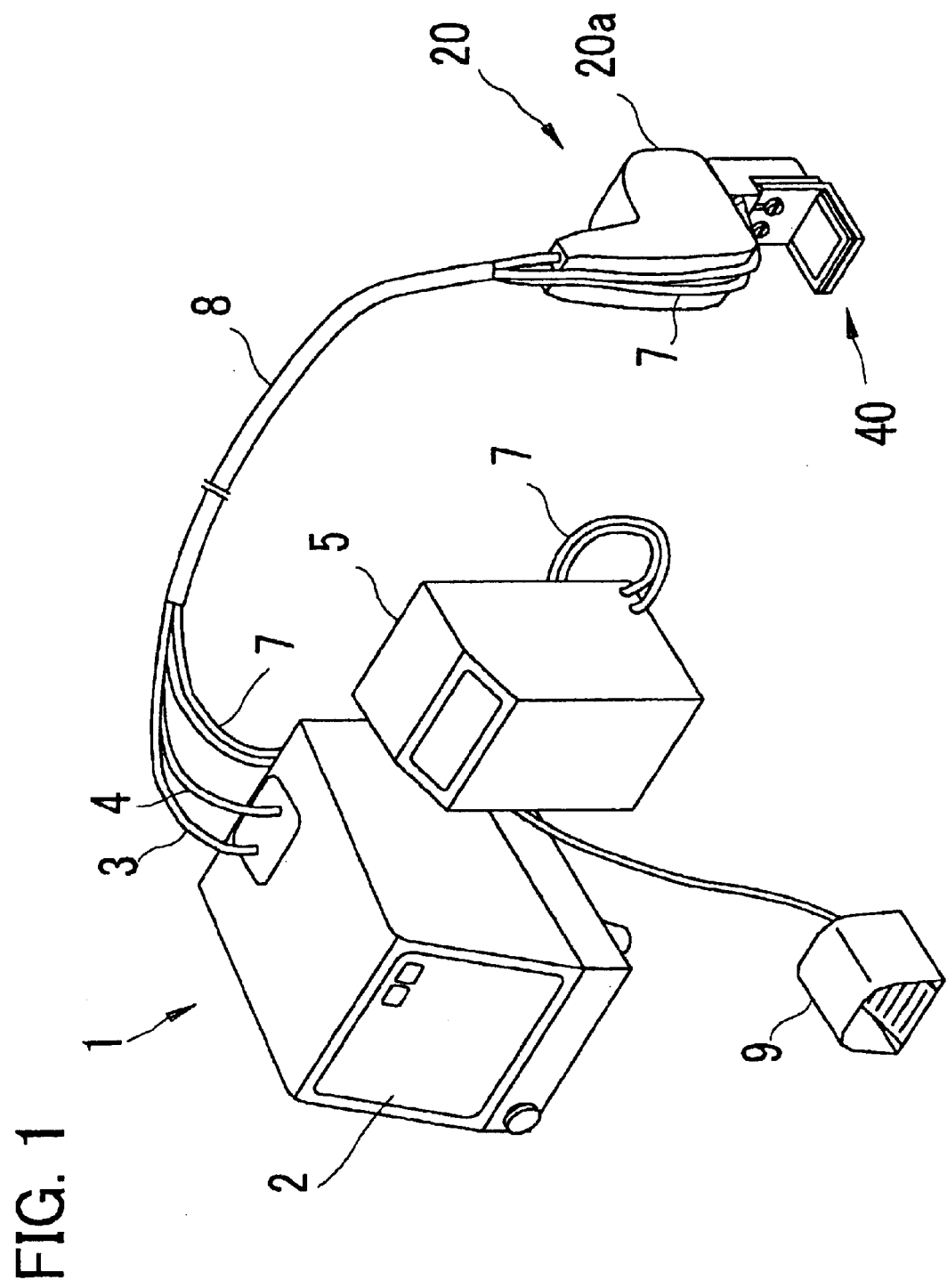
FIG. 1 is a schematic perspective view of a laser treatment apparatus in an embodiment according to the present invention.
Figure 2:
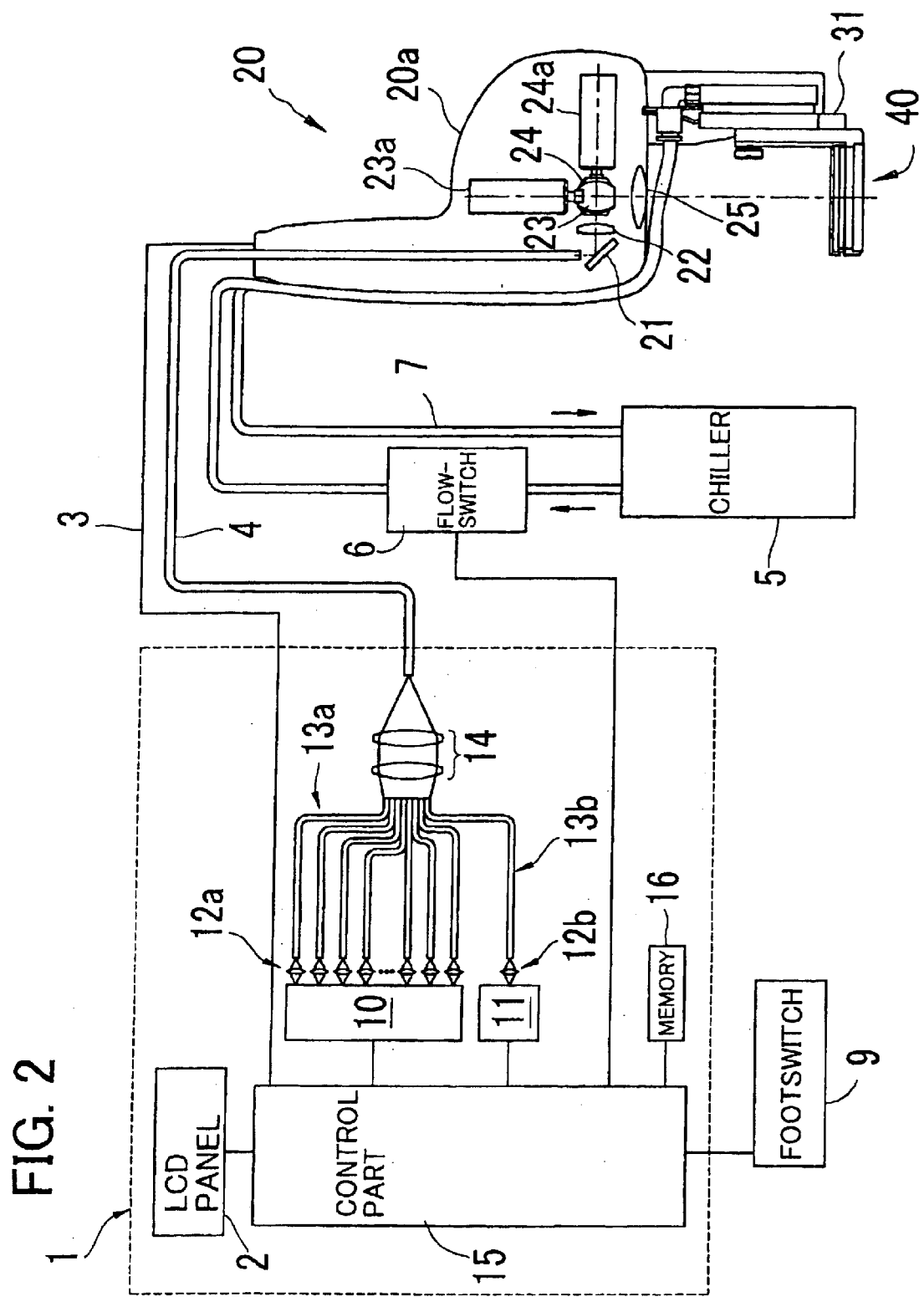
FIG. 2 is a schematic structural view of main parts of an optical system and a control system of the apparatus in the embodiment.

A detailed description of a preferred embodiment of a laser treatment apparatus embodying the present invention will now be given referring to the accompanying drawings. FIG. 1 is a schematic perspective view of the laser treatment apparatus which is used for, e.g. depilation. FIG. 2 is a schematic structural view of an optical system and a control system of the apparatus.

A main unit 1 of the apparatus is provided at the front thereof with a large-sized liquid crystal display (LCD) panel 2. This LCD panel 2 is made of a touch panel which allows an operator to make various settings with touch of operational keys or icons displayed on the panel 2. A communication cable 3 and a fiber cable 4 are provided extending from the top of the main unit 1 to a handpiece 20 for laser irradiation.

Numeral 5 is a chiller for supplying a coolant (cooling water) to the handpiece 20. Two tubes 7 extending from the chiller 5 are tied in a bundle together with the cable 3 and the fiber 4, forming a single concentration cable 8. Numeral 9 is a footswitch for generating a trigger signal to instruct execution of laser irradiation. It is to be noted that the trigger switch may be constructed of any switch different from the footswitch, e.g. a hand-switch.

In FIG. 2, numeral 10 is a laser source section for emitting laser beams for treatment and includes a plurality of semiconductor lasers (laser diodes). The laser beams emitted from the laser diodes are condensed by lenses 12a disposed in correspondence with the laser diodes and become incident on incidence end faces of fibers 13a. Exit end face sides of the fibers 13a are tied together in a bundle. The laser beams emitted from the laser diodes are thus combined together at the exit end face sides of the fibers 13a and used as a laser beam with high power for treatment. In the present embodiment, a near infrared light of wavelengths of 800 nm to 820 nm is used as a treatment laser beam.

An aiming light beam emitted from an aiming light source 11 is condensed by a condensing lens 12b and made incident on an incidence end face of a fiber 13b. An exit end face of the fiber 13b is tied in a bundle together with the exit end faces of the fibers 13a. The aiming beam discharged from the fiber 13b is allowed to go along the same optical path as that of the treatment beam. The aiming beam used in the present embodiment is a red visible light of wavelengths of 620 nm to 650 nm.

The treatment beam and the aiming beam discharged from the exit end faces (a fiber bundle part) of the fibers 13a and 13b tied together are condensed through a group of condensing lenses 14, thus becoming incident on the fiber cable 4. Through this fiber cable 4, which is connected to the handpiece 20, the beams are delivered to the handpiece 20.

A scanner head 20a of the handpiece 20 is internally provided with a first mirror 23 and a second mirror 24. These first and second mirrors 23 and 24 are rotated (swung) by a first galvano meter 23a and a second galvano meter 24a respectively, thereby shifting an irradiation position of each beam in an X-direction and a Y-direction to scan a wide area. Each beam having delivered into the scanner head 20a through the fiber cable 4 is deflected by a mirror 21 and collimated by a collimator lens 22. Subsequently, each collimated beam is deflected in the X- and Y-directions by the first and second mirrors 23 and 24. Each beam is shaped into a circular spot light having a diameter of about 5 mm by a condensing lens 25 and irradiated to the treatment part.

Figure 3:
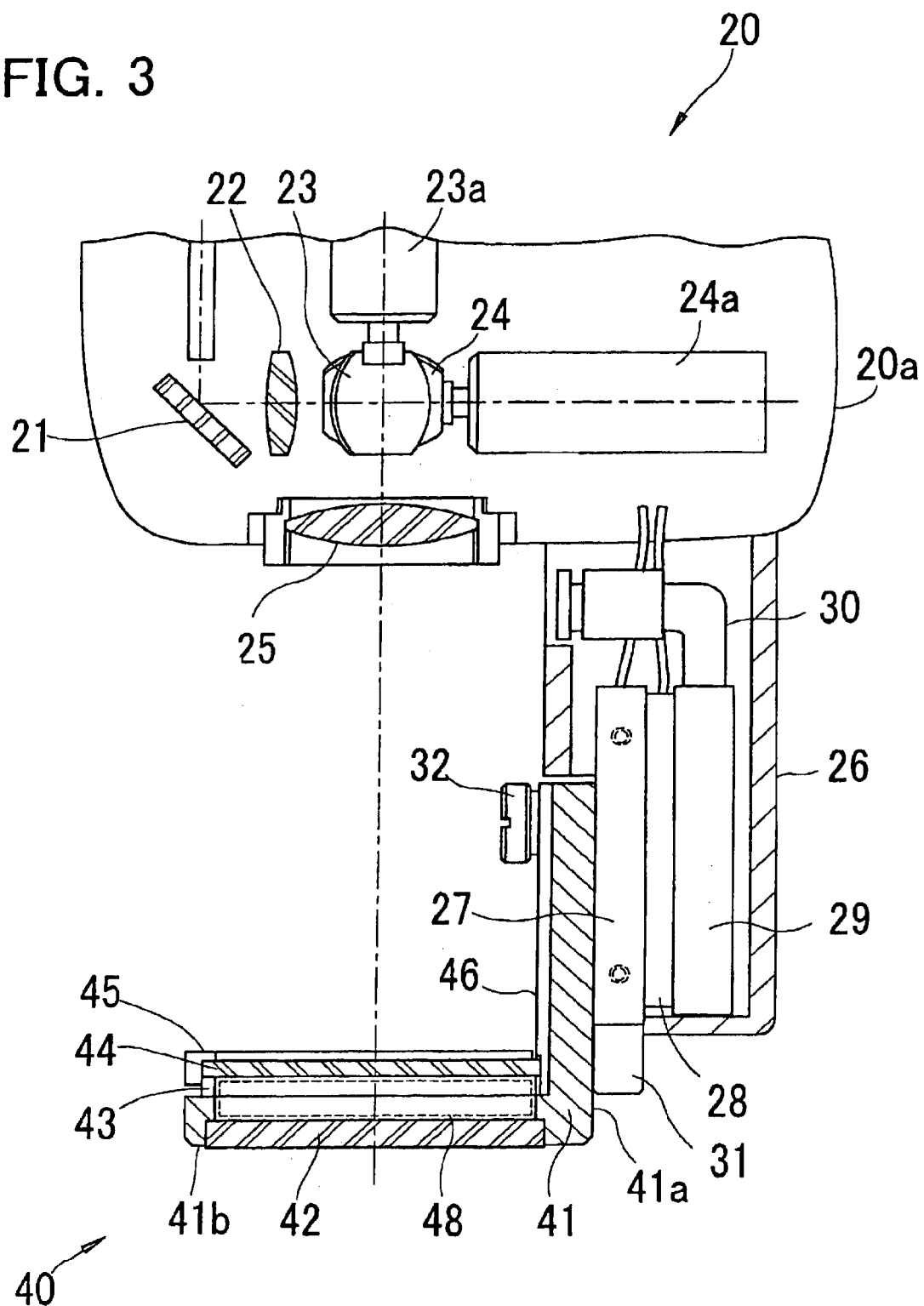
FIG. 3 is an explanatory sectional view of a part of a scanner head and a window unit of the apparatus in the embodiment.

FIG. 3 is a sectional side view of a lower part of the handpiece 20 in which a window unit 40 is attached to the underside of the scanner head 20a. The window unit 40 is replaceable with another window unit having a different size.

In FIG. 3, a scanner base 26 made of polyacetal resin having an excellent heat insulation property is fixed on the underside of the scanner head 20a. In this scanner base 26, a window attaching plate 27 made of aluminum having good thermal conductivity is secured with screws from side (in a perpendicular direction to the drawing paper of FIG. 3). Numeral 28 is a Peltier device used as an electronic heat exchanger. This Peltier device 28 is disposed in sandwich relation between a cooling plate 29 made of aluminum and the attaching plate 27. An electric current is fed through the Peltier device 28 so that one surface thereof in contact with the plate 27 serves as a heat-absorbing side (a cooling side) and the other surface in contact with the plate 29 serves as a heat-radiating side. The cooling plate 29 is internally provided with a flow passage for circulating the cooling water. The cooling water cooled in the chiller 5 is delivered through the tube 7 and a pipe 30 to the cooling plate 29 and circulated therein, which absorbs the heat radiated from the Peltier device 28 through the cooling plate 29.

Numeral 31 is a temperature sensor attached to a lower end of the attaching plate 27. This temperature sensor 31 detects the temperature of the plate 27. Based on a detection result by the sensor 31, the control part 15 controls driving of the Peltier device 28.

The window unit 40 is structured of: a first window 42 made of transparent sapphire glass having good heat conductivity, which is brought into contact with a skin for laser irradiation; a window frame 41 of a substantial L-shape in a side view for holding the first window 42; a heat insulating frame-plate 43 made of polyacetal resin having an excellent heat insulation property; a second window 44 made of transparent glass (for example, BK7 (a taxonomic code in SCHOTT Co.) generally used as optical glass) which is inferior in heat conductivity to the first window 42; and a cover 45 made of aluminum with an aperture.

The window frame 41 is made of aluminum having good thermal conductivity and includes a back plate 41a. In an upper portion of the back plate 41a, two U-shaped slots are formed. The window frame 41 is detachable/attachable with respect to the attaching plate 27 by means of two screws 32 engageable with the slots. The attaching plate 27 cooled by the Peltier device 28 cools the window frame 41, thereby cooling the first window 42.

A horizontally extending frame part 41b of the window frame 41 is formed with an aperture. On the underside of this frame part 41b, the first window 42 having a size of an about 40 mm square is attached with an adhesive having a good thermal conductivity. On the upper side of the frame part 41b, on the other hand, the second window 44 is mounted with an adhesive having a good heat insulation property through the heat insulating plate 43, thereby shielding the frame part 41b. Furthermore, a cover 45 for covering them is adhered thereon. In this configuration, an enclosed space 48 (indicated by a dotted line in FIG. 3) which serves as a heat insulating layer is produced between the first and second windows 42 and 44. This makes it possible to enhance a heat-insulating effect between both the windows forming a double-layered structure.

Numeral 46 is a heat insulating plate made of polyacetal resin for preventing the window frame 41 from absorbing heat from outside. This plate 46 is fixedly attached to the back plate 41a to insulate the second window 44 at the same time.

With the above arrangement, the heat of the skin is transmitted to the first window 42, the window frame 41, the attaching plate 27, and the Peltier device 28 in turn, and is absorbed. Thus, lowering the temperature of the first window 42 can cool the skin of a patient.

As mentioned above, the window unit 40 is attached to the lower part of the scanner head 20a. When the operator puts the first window 42 into contact with the skin, therefore, the treatment part can be uniformly flattened and the scanner head 20a can be held in a stable state. The window unit 40 is designed to have a predetermined distance between the condensing lens 25 and the undersurface of the first window 42 so that each beam discharged from the scanner head 20a is condensed on or around the undersurface of the first window 42.

In FIG. 2, the control part 15 is connected to the LCD panel 2, a flow switch 6 for monitoring whether the cooling water from the chiller 5 normally circulates, a memory 16, the footswitch 9, and others. The temperature sensor 31 provided on the handpiece 20 side, the first galvano meter 23a, the second galvano meter 24a, and the Peltier device 28 are connected to the control part 15 through the communication cable 3.

Figure 6:
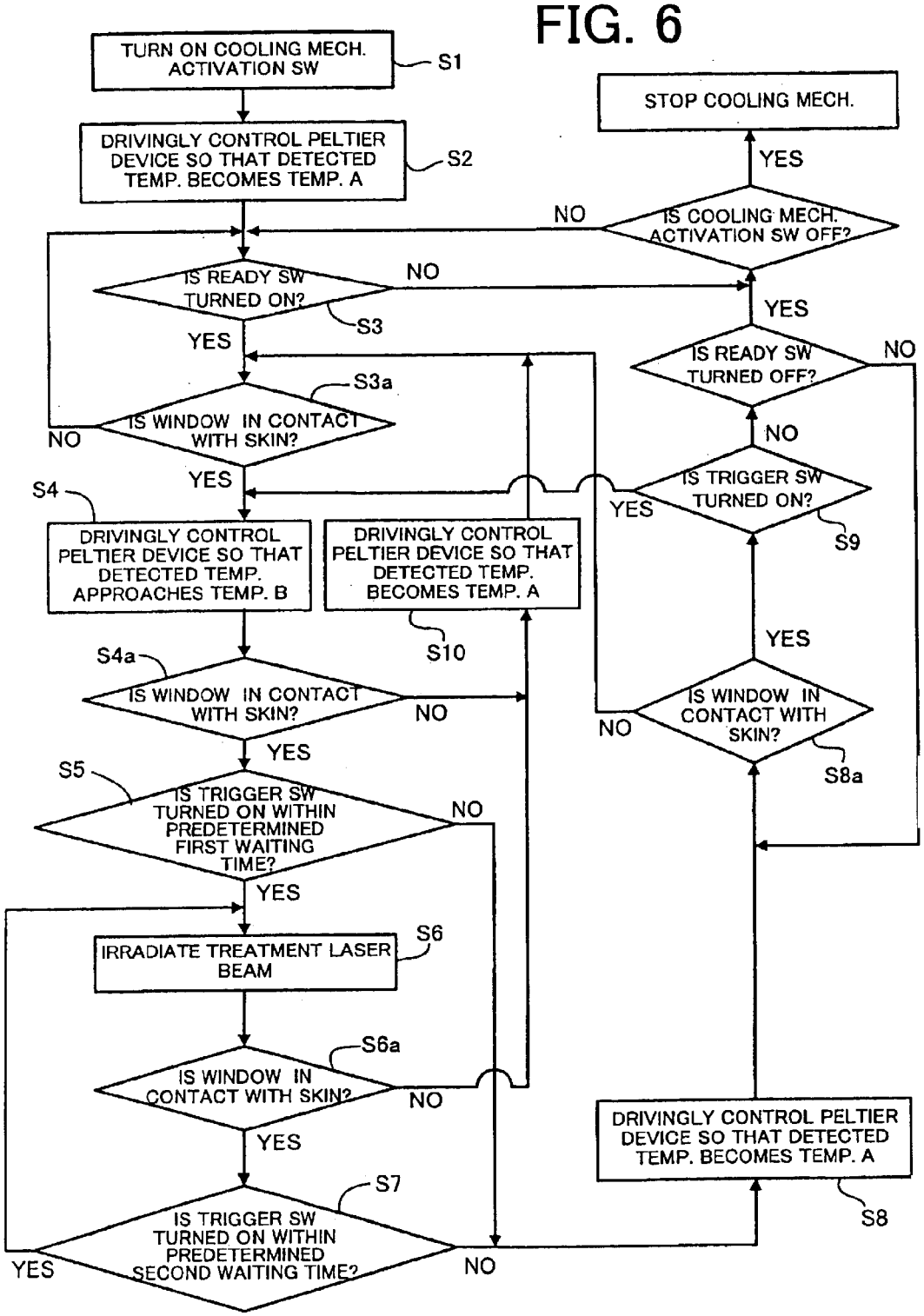
FIG. 6 is a flowchart showing an operation of the apparatus.

The operation of the laser treatment apparatus having the above structure is explained below, referring to FIG. 6.

An operator turns on a power switch of the apparatus and operates the keys on a screen of the panel 2 to activate the cooling mechanism (Step 1; "Step" will be referred to as "S"). When the Peltier device 28 and the chiller 5 are activated, the attaching plate 27, the window frame 41, and the first window 42 are cooled in turn. The control part 15 monitors detection signals from the temperature sensor 31 and drivingly controls the Peltier device 28 so that a detected temperature by the sensor 31 becomes substantially equal to a predetermined first cooling control temperature A(° C.) higher than 0° C. (S2). It is to be noted that the window 42 is not yet in contact with the skin at this time.

In this stage, the cooling control temperature is higher than 0° C., so that dew condensation occurring on the window 42 can be prevented from freezing and the condensation itself can be reduced.

Control of the Peltier device 28 is conducted by changing a driving duty ratio thereof according to a difference between the temperature A and the detected temperature. The driving duty ratio in the present embodiment means a time ratio between ON and OFF of voltage to be applied to the Peltier device 28 per unit of time. When the difference between the temperature A and the detected temperature is large (and only if the detected temperature is higher), the driving duty ratio is increased. That is, the ratio of voltage ON time per unit of time is raised.

The operator sets irradiation conditions by operation of the keys on the screen of the LCD panel 2. A laser scanning pattern is selected from patterns previously stored in the memory 16; a circular pattern, a square pattern, a rectangular pattern, a linear pattern, etc. The aiming beam is irradiated from the scanner head 20a. This aiming beam is then caused to repeatedly scan the selected pattern. The operator holds the handpiece 20 by hand to put the first window 42 into contact with the treatment part. While recognizing the affected part and an irradiation position (the scanning area) of the aiming beam observed through the windows 42 and 44, the operator adjusts the contact position of the first window 42 and sets the shape and size of the scanning pattern. As a matter of course, the laser irradiation may be performed without scanning.

Upon completion of the above preparation for irradiation including the setting of irradiation conditions, the operator turns a READY switch displayed on the screen of the panel 2 into ON to put the apparatus in a READY state. This READY state is a state that the treatment beam is irradiated when a trigger signal is input from the footswitch 9. In other words, it means the completion of preparation for laser irradiation. When the READY switch is turned into an ON state to input an operation signal to the control part 15, the control part 15 forecasts that the window 42 is in contact with the skin and the laser irradiation will be started, changes the cooling control temperature from the temperature A to a predetermined second cooling control temperature B lower than the temperature A, for example, lower by 5° C. to 30° C. than the temperature A and controls the Peltier device 28 so that the detected temperature by the temperature sensor 31 approaches the second cooling control temperature B (S4). Accordingly, the driving duty ratio of the Peltier device 28 is increased. To be more specific, a cooling power of the first window 42 is enhanced nearly just before the laser irradiation.

In the present embodiment, the temperature B means a cooling control temperature at which the window 42 can be cooled enough to prevent a burn and the like on the skin during laser irradiation when the window 42 is brought into contact with the skin. The temperature A means a cooling control temperature which can be promptly shifted to the temperature B.

Even if the cooling control temperature is changed to the temperature B, the control part 15 returns the cooling control temperature to the temperature A (S8) unless the footswitch 9 is actually pressed to generate the trigger signal within a predetermined time period (a first waiting time; e.g. 1 min.) from the input of the operation signal, thereby preventing so excessive cooling as to cause freeze of the dew condensation occurring on the window surface.

Upon receipt of the trigger signal (S5), the control part 15 drivingly controls the first and second galvanometers 23a and 24a to cause the treatment beam to scan and irradiate the selected scanning area (S6). When the laser irradiation to the scanning area first selected is completed, the operator successively advances the laser irradiation to a next scanning area.

If a trigger signal is continuously input to the control part 15 within a predetermined time period (a second waiting time; e.g. 1 min.) from the input of the previous trigger signal (S7), the control part 15 forecasts that the laser irradiation will be continued and keeps the cooling control temperature at the temperature B. To be more specific, the driving duty ratio of the Peltier device 28 is raised as compared with in the case that the cooling control temperature is set at the temperature A. In this case, even if the cooling control temperature is set at 0° C. or less, dew will not freeze on the window 42 because the window 42 has been warmed by frequent contact with the skin.

Figure 4:
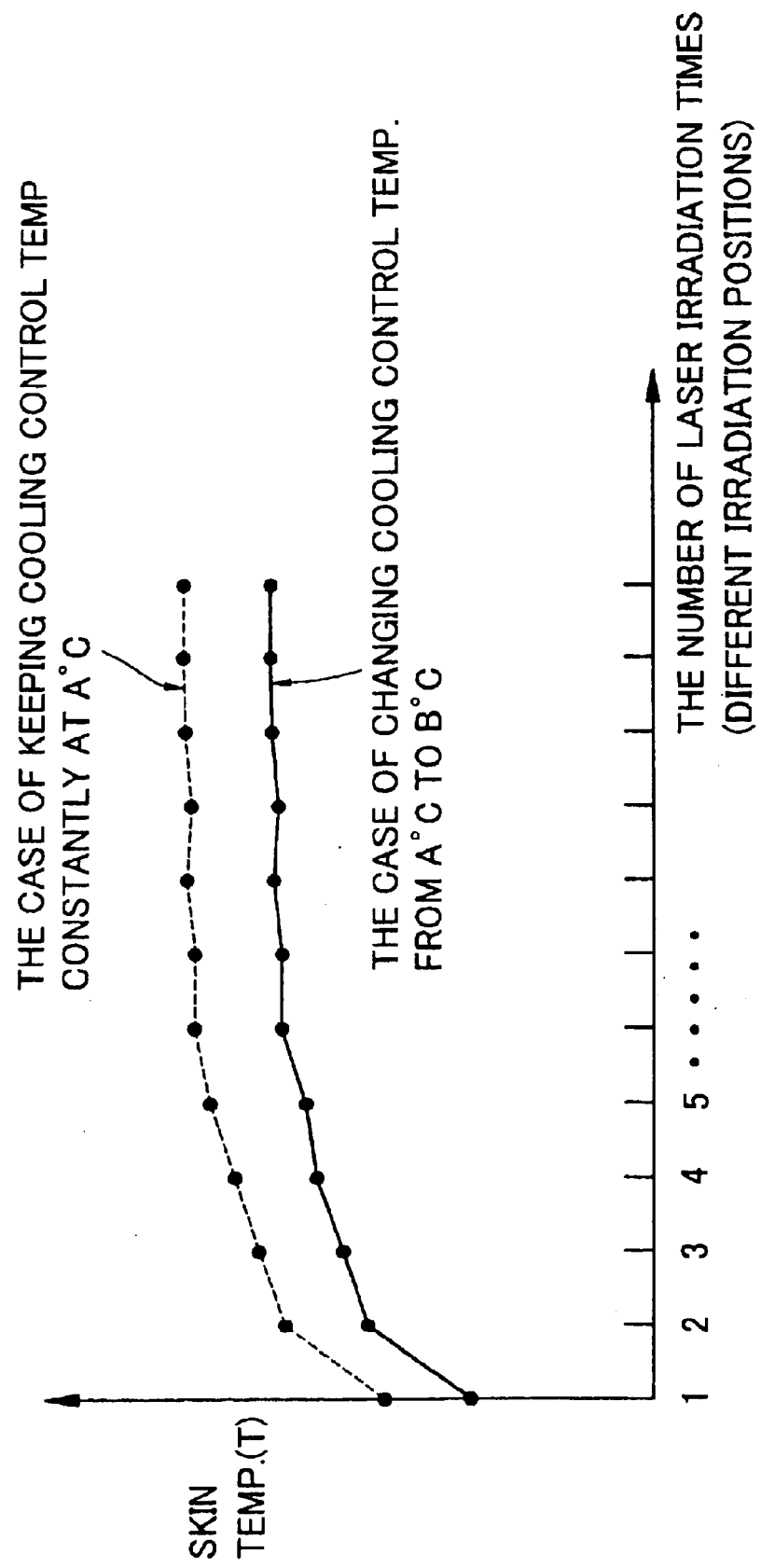
FIG. 4 is a graph showing a skin temperature varying when a laser irradiation position is sequentially changed.

FIG. 4 is a graph showing a skin temperature varying when a laser irradiation position is sequentially changed every time the laser irradiation is performed under the above control on the Peltier device 28. When the control according to the invention is applied as shown in FIG. 4 (a solid line in the graph), the skin temperature could be more lowered than in the case where the cooling control temperature was constantly kept at the temperature A (a dotted line in the graph). Thus, a pain in the treatment part during the laser irradiation could be mitigated.

When input of the trigger signal is stopped for the predetermined second waiting time or more for some reason that for example the operator stops the laser irradiation, the control part 15 forecasts that the laser irradiation will not be performed soon and therefore returns the cooling control temperature to the temperature A (S8). This makes it possible to prevent excessive cooling of the window 42 at the temperature B. As a result, the window surface can be prevented from being frozen.

When the trigger signal is input again after the cooling control temperature is returned to the temperature A (S9), the control part 15 changes the cooling control temperature to the temperature B again (S4), enhancing the cooling power of the first window 42.

In the present embodiment explained above, the cooling control temperature is returned to the temperature A if no trigger signal is input for the predetermined first and second waiting times or more. Preferably, these time settings may be arbitrarily changed by operation of the keys on the screen of the panel 2. The first waiting time and the second waiting time may be determined to be equal. The temperatures A and B themselves may arbitrarily be set by operation of the keys on the screen of the panel 2.

The window cooling mechanism, which is not limited to the above embodiment, may be arranged to cool the skin by directly circulating cooling water in which an antifreeze solution is mixed or cooling solution having a lower freezing point through the window part (window 42 and others). It is clear that this arrangement allows the same control as mentioned above.

The above control can also be executed by indirectly detecting whether or not the window 42 is in contact with the skin based on the detected result by the temperature sensor 31. In other words, when the window 42 is in noncontact with the skin after activation of the cooling mechanism, the detected temperature by the temperature sensor 31 becomes substantially stable at the temperature A. When the window 42 is then brought into contact with the skin, the detected temperature by the temperature sensor 31 increases. When this detected temperature exceeds a predetermined level, the control part 15 judges that the window 42 has been made contact with the skin (S3a) and changes the cooling control temperature to the temperature B (S4). When the window 42 is repeatedly brought into contact with the skin, the detected temperature by the sensor 31 will be maintained at a temperature lower than the temperature A and higher than the temperature B. Then, as time passes after stop of the contact with the skin, the detected temperature largely decreases or becomes substantially equal to the temperature B. The control part 15 judges, at this time, that the window 42 is in noncontact with the skin (S4a, S6a, and S8a) and thus controls the Peltier device 28 to return the cooling control temperature to the temperature A (S10). In this case, if it is judged again that the window 42 is in contact with the skin (S3a), the control part 15 changes the cooling control temperature to the temperature B (S4) again, enhancing the cooling power of the window 42.

It is to be noted that the cooling control temperature control based on detection of the contact with a skin may be limited to the case where the cooling control temperature is changed from the temperature A to the temperature B (S3a). The detection of the contact with a skin may be combined with operation of the READY switch. Moreover, the laser irradiation may be controlled based on the detection whether the window 42 is in contact with a skin (the laser irradiation is disabled when the window 42 is in noncontact with the skin).

Figure 5:
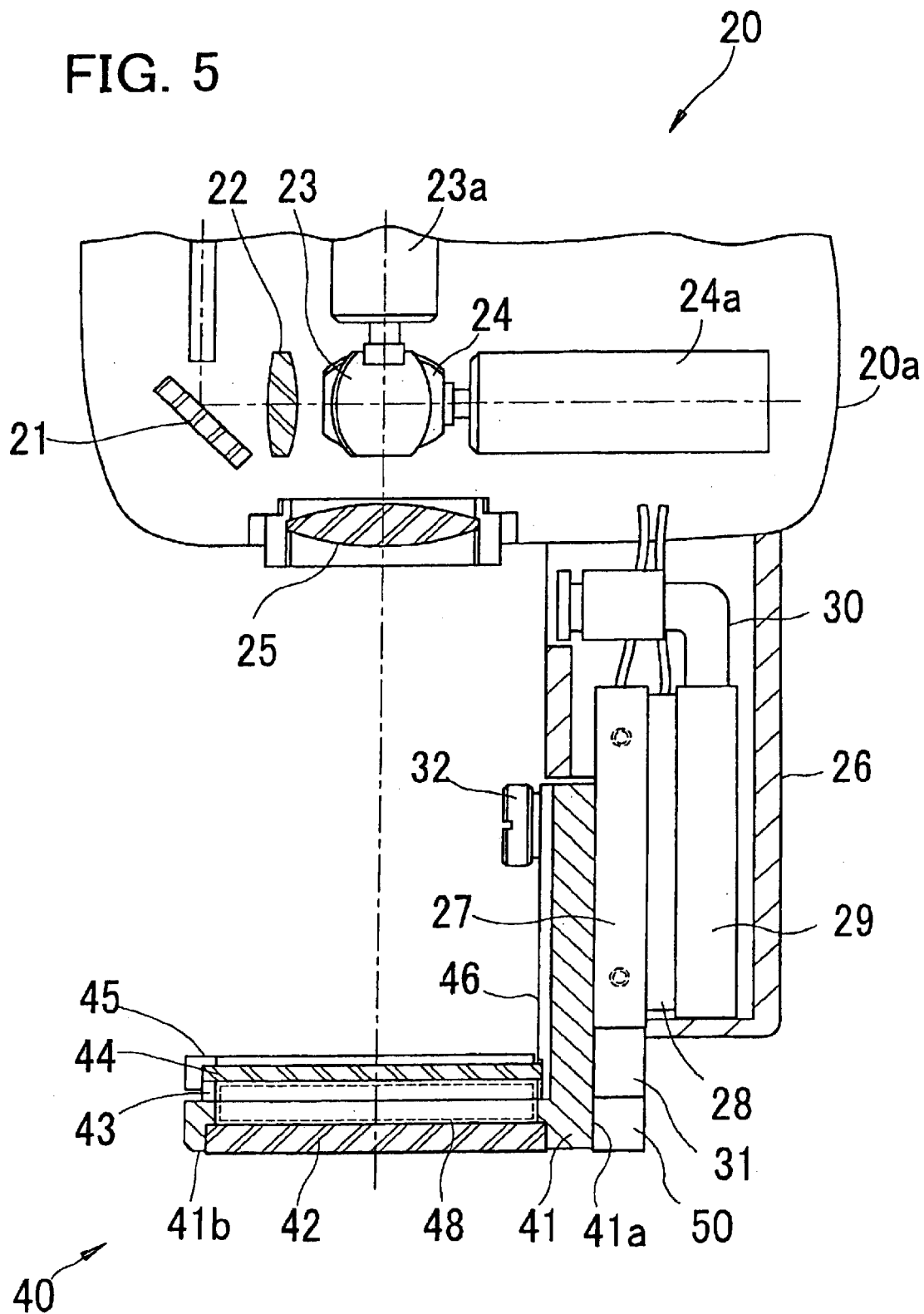
FIG. 5 is a sectional view of a part of the scanner head and a window unit with a touch sensor.

The above explanation is an example of indirectly detecting the contact state of the window 42 with respect to the skin. Additionally, a detecting means of directly detecting the contact state with the skin may be provided. FIG. 5 shows this example, in which a touch sensor 50 is attached under the temperature sensor 31 so that an undersurface of the touch sensor 50 is substantially flush with the undersurface of the window 42 which is brought into contact with the skin. The touch sensor 50 thus directly detects the contact state of the window 42 with the skin. Based on the detected result by the sensor 50, the control part 15 sets the cooling control temperature changeably between the temperatures A and B.

The temperature sensor may be constructed as a sensor which directly detects the temperature of the window 42 or a sensor which detects the temperature of the window frame 41. The position where the temperature sensor is disposed is not limited in particular. According to the distance from and the positional relation with the Peltier device 28, the cooling control temperature is appropriately determined.

As explained above, according to the present invention, the laser irradiation can be executed while cooling the affected part and preventing the occurrence of due condensation and freezing on the window surface. This can reduce thermal damage to the affected part.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus for performing treatment on a treatment part of a skin by irradiating the part with a laser beam for treatment, the apparatus including:

a window having an optical property of transmitting the treatment beam, the window adapted to be brought into contact with the skin for laser irradiation;

a window cooling unit;

contact-state detecting means which detects a contact state of the window with the skin; and control means which changes a cooling control temperature of the cooling unit, at which the cooling unit is maintained from a predetermined first temperature which is previously set higher than 0° C. to a predetermined second temperature which is previously set lower than 0° C. when the contact-state detecting means detects that the window is in contact with the skin.

2. The laser treatment apparatus according to claim 1, wherein the control means returns the cooling control temperature to the first temperature when the contact-state detecting means detects that the window is in noncontact with the skin after the cooling control temperature is changed to the second temperature.

3. The laser treatment apparatus according to claim 1, wherein the contact-state detecting means includes a touch sensor having a contact surface substantially flush with a contact surface of the window.

4. The laser treatment apparatus according to claim 1, further including a temperature sensor which detects a temperature of the window or the cooling unit, wherein the contact-state detecting means detects the contact state based on a detection result by the temperature sensor.

5. The laser treatment apparatus according to claim 1, further including a temperature sensor which detects a temperature of the window or the cooling unit, wherein the control means controls the cooling unit based on detection results by the contact-state detecting means and the temperature sensor.

6. The laser treatment apparatus according to claim 1, further including input means which inputs a laser irradiation command signal, wherein the control means returns the cooling control temperature to the first temperature when no irradiation command signal is input by the input means within a predetermined waiting time after the cooling control temperature is changed to the second temperature.

7. The laser treatment apparatus according to claim 6, further including time setting means which variably sets the waiting time.

8. The laser treatment apparatus according to claim 1, further including temperature setting means which variably sets at least one of the first temperature and the second temperature.

9. The laser treatment apparatus according to claim 1, wherein the cooling unit is a Peltier element.

10. The laser treatment apparatus according to claim 1, wherein the second temperature is previously set lower by 5° C. to 30° C. than the first temperature.

11. A laser treatment apparatus for performing treatment on a treatment part of a skin by irradiating the part with a laser beam for treatment, the apparatus including:
 a window having an optical property of transmitting the treatment beam, the window adapted to be brought into contact with the skin for laser irradiation;
 a window cooling unit;
 first input means which inputs an operation signal representing that preparation for laser irradiation is completed; and
 control means which changes a cooling control temperature of the cooling unit, at which the cooling unit is maintained, from a predetermined first temperature which is previously set higher than 0° C. to a predetermined second temperature which is previously set lower than 0° C. when the operation signal is input by the first input means.

12. The laser treatment apparatus according to claim 11, further including contact-state detecting means which detects a contact state of the window with the skin,
 wherein the control means returns the cooling control temperature to the first temperature when the contact-state detecting means detects that the window is in noncontact with the skin after the cooling control temperature is changed to the second temperature.

13. The laser treatment apparatus according to claim 12, wherein the control means changes the cooling control temperature to the second temperature when the contact-state detecting means detects that the window is in contact with the skin while the cooling control temperature is at the first temperature.

14. The laser treatment apparatus according to claim 11, further including a temperature sensor which detects a temperature of the window or the cooling unit,
 wherein the control means controls the cooling unit based on a presence/absence of input of the operation signal and a detection result by the temperature sensor.

15. The laser treatment apparatus according to claim 11, further including second input means which inputs a laser irradiation command signal,
 wherein the control means returns the cooling control temperature to the first temperature when no irradiation command signal is input within a predetermined waiting time after the tooling control temperature is changed to the second temperature.

16. The laser treatment apparatus according to claim 15, further including time setting means which variably sets the waiting time.

17. The laser treatment apparatus according to claim 11, further including temperature setting means which variably sets at least one of the first temperature and the second temperature.

18. The laser treatment apparatus according to claim 11, wherein the cooling unit is a Peltier element.

19. The laser treatment apparatus according to claim 11, wherein the second temperature is previously set lower by 5° C. to 30° C. than the first temperature.

20. A laser treatment apparatus for performing treatment on a treatment part of a skin by irradiating the part with a laser beam for treatment, the apparatus including:
 a window having an optical property of transmitting the treatment beam, the window adapted to be brought into contact with the skin for laser irradiation;
 a window cooling unit;
 irradiation command signal input means which inputs a laser irradiation command signal;
 temperature change signal input means which inputs a temperature changing signal to change a cooling control temperature of the cooling unit from a predetermined first temperature higher than 0° C. to a predetermined second temperature lower than the first temperature; and
 control means which changes the cooling control temperature from the first temperature to the second temperature in response to the temperature changing signal input by the temperature change signal input means and returns the cooling control temperature to the first temperature when no irradiation command signal is input by the irradiation command signal input means within a predetermined waiting time after the cooling control temperature is changed to the second temperature.

21. The laser treatment apparatus according to claim 20, further including time setting means which variably sets the waiting time.

22. The laser treatment apparatus according to claim 20, further including temperature setting means which variably sets at least one of the first temperature and the second temperatures.

23. The laser treatment apparatus according to claim 20, wherein the cooling unit is maintained at the cooling control temperature.

24. The laser treatment apparatus according to claim 23, wherein the cooling unit is a Peltier element.

25. The laser treatment apparatus according to claim 20, wherein the second temperature is previously set lower than 0° C.

26. The laser treatment apparatus according to claim 20, wherein the second temperature is previously set lower by 5° C. to 30° C. than the first temperature.

* * * * *